(12) United States Patent
Stad et al.

(10) Patent No.: US 9,131,967 B2
(45) Date of Patent: Sep. 15, 2015

(54) SYSTEM AND METHOD OF MANIPULATING SPINAL CONSTRUCTS

(71) Applicant: DePuy Synthes Products, Inc., Raynham, MA (US)

(72) Inventors: Shawn D. Stad, Raynham, MA (US); Garth G. Baker, Raynham, MA (US); Douglas Lothrop, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 15 days.

(21) Appl. No.: 13/926,138

(22) Filed: Jun. 25, 2013

(65) Prior Publication Data
US 2014/0039557 A1  Feb. 6, 2014

Related U.S. Application Data

(62) Division of application No. 11/950,739, filed on Dec. 5, 2007, now Pat. No. 8,491,590.

(51) Int. Cl.
*A61B 17/70* (2006.01)

(52) U.S. Cl.
CPC ............ *A61B 17/708* (2013.01); *A61B 17/7077* (2013.01)

(58) Field of Classification Search
CPC ................................................. A61B 17/7077
USPC ............................................... 606/279, 86 A
See application file for complete search history.

(56) References Cited

U.S. PATENT DOCUMENTS

| 4,299,368 | A | 11/1981 | Winkler |
|---|---|---|---|
| 5,531,751 | A | 7/1996 | Schultheiss et al. |
| 6,090,113 | A | 7/2000 | Le Couedic et al. |
| 6,551,316 | B1 | 4/2003 | Rinner et al. |
| 6,969,392 | B2 | 11/2005 | Gitis et al. |
| 7,008,432 | B2 | 3/2006 | Schlapfer et al. |
| 2003/0135220 | A1 | 7/2003 | Cauthen |
| 2004/0024411 | A1 | 2/2004 | Newton et al. |
| 2004/0210232 | A1 | 10/2004 | Patel et al. |
| 2005/0015092 | A1 | 1/2005 | Rathbun et al. |
| 2005/0021040 | A1 | 1/2005 | Bertagnoli |
| 2005/0273167 | A1 | 12/2005 | Triplett et al. |
| 2006/0004380 | A1 | 1/2006 | DiDomenico et al. |
| 2006/0069391 | A1* | 3/2006 | Jackson .......................... 606/62 |
| 2006/0095035 | A1 | 5/2006 | Jones et al. |
| 2006/0111715 | A1 | 5/2006 | Jackson |
| 2006/0195114 | A1 | 8/2006 | Bertagnoli |
| 2006/0217735 | A1 | 9/2006 | MacDonald et al. |
| 2008/0009863 | A1 | 1/2008 | Bond et al. |
| 2008/0015601 | A1 | 1/2008 | Castro et al. |
| 2009/0149892 | A1 | 6/2009 | Stad et al. |
| 2010/0036443 | A1* | 2/2010 | Hutton et al. ............... 606/86 R |

* cited by examiner

*Primary Examiner* — Ellen C Hammond
(74) *Attorney, Agent, or Firm* — Nutter McClennen & Fish LLP

(57) ABSTRACT

Systems of manipulating (e.g., compressing or distracting) a spinal construct are provided herein. In general, the system can include a surgical sleeve extending from a vertebra and a fulcrum movably coupled to some component of the system thereby allowing the fulcrum to be positioned at various location along the length of the sleeve. As indicated, the fulcrum can be movably coupled to virtually any component of the system. For example, the fulcrum can be movably coupled to the surgical sleeve, to a manipulation device sized and configured to receive the surgical sleeve, to a driver configured to apply a manipulation force, etc. Additionally, methods for manipulating a spinal construct are also provided herein.

15 Claims, 18 Drawing Sheets

SYSTEM AND METHOD OF MANIPULATING SPINAL CONSTRUCTS

FIELD OF USE

This is a divisional application of co-pending U.S. patent application Ser. No. 11/950,739, filed on Dec. 5, 2007, which is herein incorporated by reference in its entirety.

BACKGROUND

For numerous reasons, spinal fixation devices are used in spinal surgery to align and/or fix a desired relationship between adjacent vertebral bodies. Such devices typically include a spinal fixation element, such as a relatively rigid fixation rod or plate, that is coupled to adjacent vertebrae by attaching the element to various anchoring devices, such as hooks, bolts, wires, or screws. The fixation element can have a predetermined contour that has been designed according to the properties of the target implantation site, and once installed, the fixation element can hold the vertebrae in a desired spatial relationship, either until desired healing or spinal fusion has taken place, or for some longer period of time.

In use, a spinal fixation element can be anchored to specific portions of a vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screw assemblies typically include a threaded shank capable of being positioned within a vertebra, and a head portion having a rod-receiving element, usually in the form of a U-shaped recess. A set-screw, plug, or similar type of closure mechanism can be used to secure the fixation element, e.g., a spinal rod, into the rod-receiving head of the pedicle screw.

Often, such fixation procedures will require some degree of manipulation of adjacent vertebrae (e.g., compression or distraction) in order to properly position the fixation element and/or to achieve the desired therapeutic effect. However, these manipulation steps can be cumbersome as the working area tends to be crowded and the required instrumentation can be difficult to position, adjust, and/or maintain at a desired location. Thus, there remains a need for systems and methods of manipulating spinal constructs.

SUMMARY

Systems and methods of manipulating (e.g., distracting or compressing) a spinal construct are provided herein. More specifically, the presently disclosed systems and methods simplify a surgeon's ability to manipulate spinal construct(s) by providing an adjustable fulcrum disposed between first and second surgical sleeves (e.g., percutaneous access devices) extending from adjacent vertebrae. As described below, various embodiments of such a fulcrum can be movably coupled to any of a number of components. For example, the fulcrum can be coupled to either of the surgical sleeves extending from the adjacent vertebrae or the fulcrum can be coupled to a manipulation device configured for placement over such a surgical sleeve. In another example, the fulcrum can be coupled to a manipulation instrument capable of applying a desired manipulation force either above or below the secured fulcrum thereby resulting in distraction or compression of the spinal construct, respectively. In other embodiments, the system can include additional sleeves (e.g., an anti-torque sleeve) capable of further simplifying the procedure. The system can also be configured to allow for various constraints of a patient's anatomy (e.g., close spacing between vertebrae) while performing such a procedure. Other such benefits and advantages of the presently disclosed system and method will be evident from the following disclosure.

Various aspects of a system for manipulating a spinal construct are provided herein. In one aspect, a spinal manipulation system is provided which can include a sleeve having a proximal end, a distal end, and an inner lumen extending therebetween. Further, the system can include a fulcrum releasably coupled to the sleeve such that the fulcrum can be selectively positioned at a desired level on the sleeve. Various embodiments of such a sleeve are included within the scope of the presently disclosed system. For example, the sleeve can be any type of surgical sleeve (e.g., a percutaneous access device) having a distal end configured to engage a bone anchor positioned within a vertebra. In other embodiments, the sleeve can be a manipulation device having an inner lumen sized and configured to receive such a surgical sleeve.

Various embodiments of such a manipulation device are provided herein. For example, the manipulation device can have a distal end having an indentation configured to receive a spinal fixation element formed in the outer surface of the device. In other embodiments, the manipulation device can include a proximal end which is configured to releasably engage a proximal end of a surgical sleeve. In such an embodiment, the proximal end of the device can further include at least one flat region corresponding to a flat region formed on the proximal end of the surgical sleeve. Thus, the distal indentation and/or the proximal flat region can prevent rotation/twisting of the manipulation device relative to the surgical sleeve.

The system can also include a fulcrum capable of being positioned at any of a plurality of locations relative to first and second surgical sleeves extending from adjacent vertebrae. As described below, the fulcrum can be virtually any element capable of providing the desired therapeutic effect. For example, the fulcrum can be a substantially cylindrical element having first and second ends with a longitudinal axis extending therebetween. In such an example, the fulcrum can be coupled to the sleeve such that the longitudinal axis of the fulcrum is substantially perpendicular to a longitudinal axis of the surgical sleeve. Additionally, the fulcrum can include a first actuator coupled to the first end and (optionally) a second actuator coupled to the second end wherein the first and second actuators are biased (e.g., via a spring) such that in the absence of an actuation force the fulcrum can remain securely engaged to a desired location (e.g., engagement point) of the sleeve. The fulcrum can be sized to allow at least one of adjacent surgical sleeves to pivot about the fulcrum in response to a manipulation force. In some embodiments, the diameter of the fulcrum can be increased as required by the given procedure and/or the patient's anatomy. For instance, in one such embodiment, any of a plurality of inserts can be secured to the fulcrum thereby increasing the diameter a desired amount.

As described below, the fulcrum can be movably coupled to the sleeve in various manners. For example, in one embodiment, the sleeve (e.g., any type of surgical sleeve or a manipulation device sized and configured to receive the surgical sleeve) can include a plurality of engagement points configured to releasably engage the fulcrum extending along a length of the sleeve. In another embodiment, the fulcrum can be releasably engaged to a cap configured to be positioned over a proximal end of the surgical sleeve. As will be shown, the cap can extend any desired length along the surgical sleeve thereby positioning the fulcrum at any desired location relative to the adjacent surgical sleeves. In one embodiment, a kit can also be provided which can include a plurality of such caps having various lengths.

In other embodiments, the system can include various additional types of accessory sleeves capable of providing additional therapeutic effects. For example, the system can include an anti-torque sleeve coupled to a second surgical sleeve located adjacent the first surgical sleeve. In an exemplary embodiment, the anti-torque sleeve can include a proximal end, a distal end, and an inner lumen extending therebetween wherein the inner lumen of the sleeve is sized and configured to receive the second surgical sleeve (e.g., a second percutaneous access device). In such an embodiment, the anti-torque sleeve (optionally having a handle extending therefrom) can facilitate delivery of a closure mechanism (e.g., a set screw, a plug, or a pin) to a bone anchor corresponding to the second surgical sleeve. Thus, use of the anti-torque sleeve can allow for the fixation element to be secured almost immediately following the compression or distraction procedure.

In another aspect, a spinal manipulation system is provided which includes a first surgical sleeve extending from a first vertebra, a second surgical sleeve extending from a second vertebra, and a driver configured to supply a manipulation force to the adjacent surgical sleeves. Further, the system can include a fulcrum movably coupled to any of the first or second surgical sleeves, or the fulcrum can be movably coupled to the driver. In any of these examples, the fulcrum can be selectively positioned at a desired level relative to the first and second surgical sleeves. When the fulcrum is movably coupled to the driver, the fulcrum can be adjusted between an extended position distal of a pair of forceps of the driver, and a retracted position proximal of the pair of forceps. Thus, the surgeon can adjust the relative position of the fulcrum to the forceps depending on the desired manipulation (e.g., compression or distraction). In another embodiment, similar to above, the fulcrum can be coupled to a cap releasably positioned over a proximal end of one of the surgical sleeves. Also similar to above, the system can include a manipulation device having a proximal end, a distal end, and an inner lumen extending therebetween wherein the inner lumen is sized and configured to receive either of the surgical sleeves. Additionally, the manipulation sleeve can include a plurality of engagement points configured to releasably engage the fulcrum extending along a length thereof.

In yet another aspect, a spinal manipulation system is provided which includes an elongate sleeve having a proximal end, a distal end, and an inner lumen extending therebetween wherein the inner lumen is sized and configured to be positioned over a surgical sleeve. Additionally, the elongate sleeve can include an engagement track having a plurality of engagement points formed at distinct locations along a length of the sleeve. The system can also include a fulcrum configured to releasably engage any of the plurality of the engagement points. Like above, the fulcrum can be slidably coupled to the engagement track.

Various aspects of a method for manipulating a spinal construct are also provided herein. In one aspect, the method includes engaging a first surgical sleeve to a first bone anchor disposed within a first vertebra and engaging a second surgical sleeve to a second bone anchor disposed within a second vertebra located adjacent the first vertebra. Next, the method can include installing a spinal fixation element such that at least a portion of the fixation element resides within the first and second bone anchors. The method further includes applying a manipulation force to the first and second surgical sleeves by a driver. As detailed below, the manipulation force can pivot one of the surgical sleeves around the fulcrum which, similar to the embodiments summarized above, can be movably coupled with any of the first surgical sleeve, the second surgical sleeve, a manipulation device, or a driver.

As described below, the location of the fulcrum relative to the location of the applied manipulation force can be adjusted to effect compression or distraction and also the amount of compression or distraction so provided. For example, in one embodiment, the manipulation force can be applied above the fulcrum to effect distraction of a spinal construct, while in other embodiments the manipulation force can be applied below the fulcrum to effect compression of the construct. Additionally, the distance above or below the fulcrum to which the force is applied can determine the amount of force provided. Also like above, the method can include coupling a manipulation device to the first surgical sleeve wherein the fulcrum is movably coupled to the manipulation device. Additionally, the method can further include coupling an anti-torque sleeve to the second surgical sleeve. As described below, the use of such an anti-torque sleeve can allow for a closure mechanism (e.g., a set screw, a plug, or a pin) to be almost immediately secured to the corresponding bone anchor.

In yet another embodiment, a method is provided for manipulating a spinal construct which includes engaging a surgical sleeve to a first vertebra and engaging a second surgical sleeve to a second vertebra adjacent to the first vertebra. The method can further include placing at least a portion of a spinal fixation element within first and second bone anchors coupled to the first and second surgical sleeves, respectively. The method can also include positioning a manipulation device over the first surgical sleeve. In such an embodiment, the manipulation sleeve can include a fulcrum movably (e.g., slidably) coupled thereto. Like above, such a movable coupling can allow the fulcrum to releasably engage any of a plurality of engagement points along an engagement track of the device. The method can also include securing a closure mechanism to the first bone anchor thereby securing the spinal fixation element therein. Optionally, the method can include coupling an accessory sleeve (e.g., an anti-torque sleeve) to an adjacent surgical sleeve. The method can also include releasably engaging the fulcrum to a desired engagement point along the length of the engagement track and applying a manipulation force to the adjacent sleeves. In such an embodiment, the manipulation force is capable of causing the second surgical sleeve to pivot about the fulcrum. The method can further include securing a second closure mechanism to the second bone anchor thereby securing the spinal fixation element within the second bone anchor.

In other embodiments, the method can include removing the manipulation device from the first surgical sleeve and removing the anti-torque sleeve from the second percutaneous access device. Further, the method can include repositioning the manipulation device over the second surgical sleeve and positioning the anti-torque sleeve over a third surgical sleeve having a distal portion engaged to a third bone anchor. Thus, the method can include applying a second manipulation force to the repositioned manipulation device and anti-torque sleeve thereby causing the anti-torque sleeve to once again pivot about the fulcrum. Additionally, the method can include engaging a third closure mechanism to the third bone anchor thereby securing the spinal fixation element within the third bone anchor. These steps (or at least some of them) can be repeated as many times as desired thereby effecting compression or distraction to any number of spinal constructs along a patient's a spinal column.

These aspects, as well as others, are described in detail below.

BRIEF DESCRIPTION OF THE DRAWINGS

The presently disclosed systems and methods will be more fully understood from the following detailed description taken in conjunction with the accompanying drawings, in which.

DETAILED DESCRIPTION

Figure 1A:
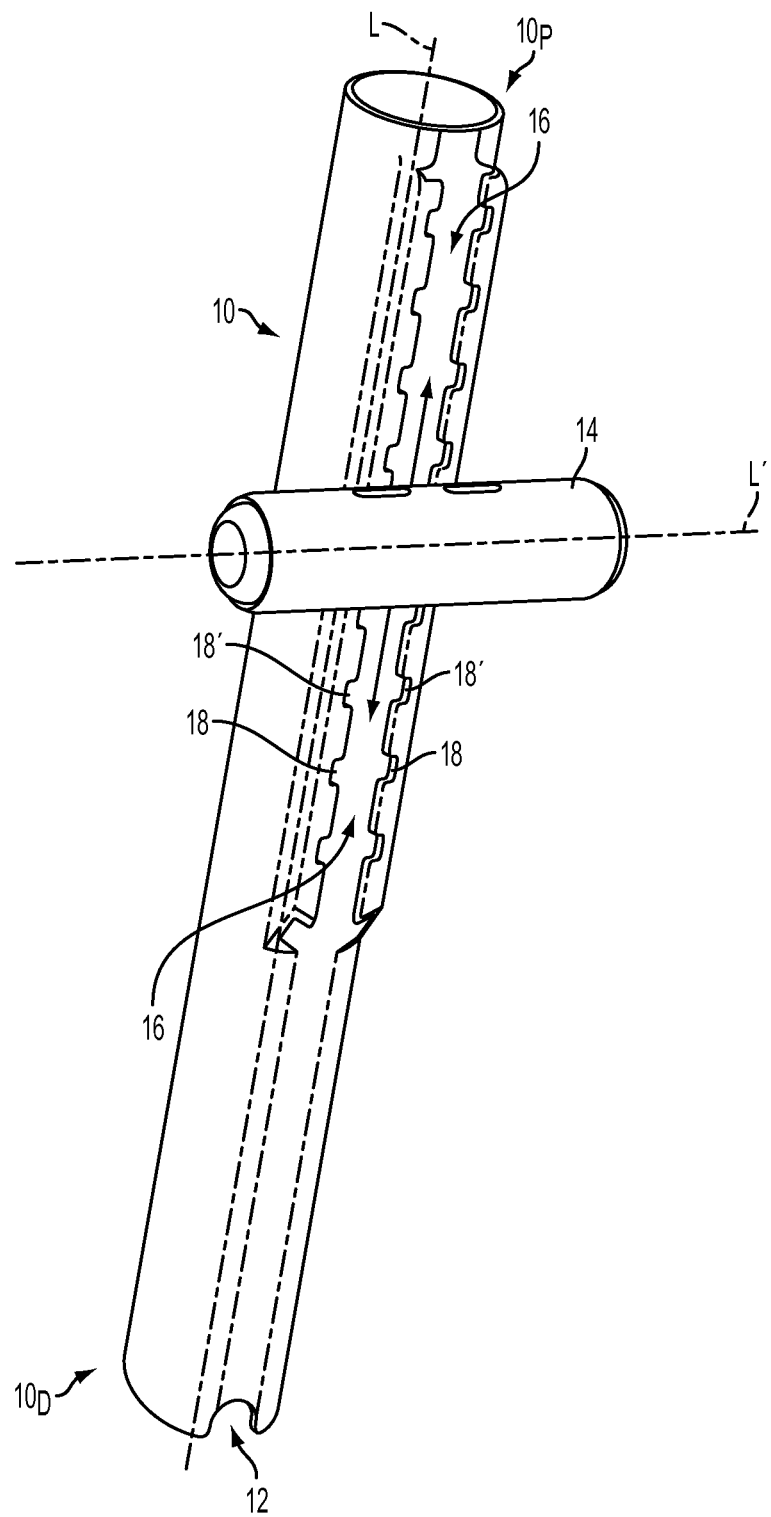
FIG. 1A is a perspective view of an exemplary embodiment of a manipulation device.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Various embodiments of a system of manipulating (e.g., compressing or distracting) a spinal construct are provided herein. In general, the presently disclosed system utilizes first and second surgical sleeves extending from adjacent vertebrae and a fulcrum that is position-adjustable and releasably engaged to some component of the system to allow one of the sleeves to pivot about the fulcrum in response to the application of a manipulation force. For example, the fulcrum can be adjusted to a desired position and releasably coupled to either of the surgical sleeves, releasably coupled to a manipulation device positioned over one of the surgical sleeves, or the fulcrum can be movably coupled to a driver capable of applying the manipulation force to the sleeves. The system can also include additional accessory sleeves (e.g., an anti-torque sleeve) that are configured to be coupled to one of the surgical sleeves. As described below, the accessory sleeve can enhance the efficiency of the system and/or provide some additional therapeutic benefit.

As stated, the system can include or work in conjunction with first and second surgical sleeves extending from adjacent vertebrae. As will be apparent to those skilled in the art, such sleeves can include virtually any device capable of releasably engaging and extending from a target vertebra. For example, as shown in FIGS. 2A-2E, at least one of the surgical sleeves 48 can be a percutaneous access device 48. In general, the percutaneous access device 48 can be any device having a distal end $48_D$ configured to releasably engage a bone anchor $B_1$, and having a length (l) such that a proximal end $48_P$ of the percutaneous access device 48 is accessible to a user. Also apparent to those skilled in the art, the bone anchor $B_1$ can include any element having a distal portion (not shown) configured to engage a vertebral bone $V_1$ (e.g., a threaded shank) and a proximal receiving head $B_P$ that can be coupled to the distal bone engaging element wherein the receiving head $B_P$ is configured to receive a fixation element 50. Further, the receiving head $B_P$ of the bone anchor $B_1$ can be configured to receive a closure mechanism (e.g., a set screw, a plug, or a pin) to secure the fixation element within the receiving head $B_P$. In an exemplary embodiment, the length (l) of the device 48 is selected such that the proximal end $48_P$ of the percutaneous access device 48 is positioned external the patient. Further, the percutaneous access device 48 can include an inner lumen extending from the proximal end $48_P$ to the distal end $48_D$ thereby providing a passageway for delivery of various instruments and/or elements (e.g., a fixation element) to the treatment site.

Figure 4A:
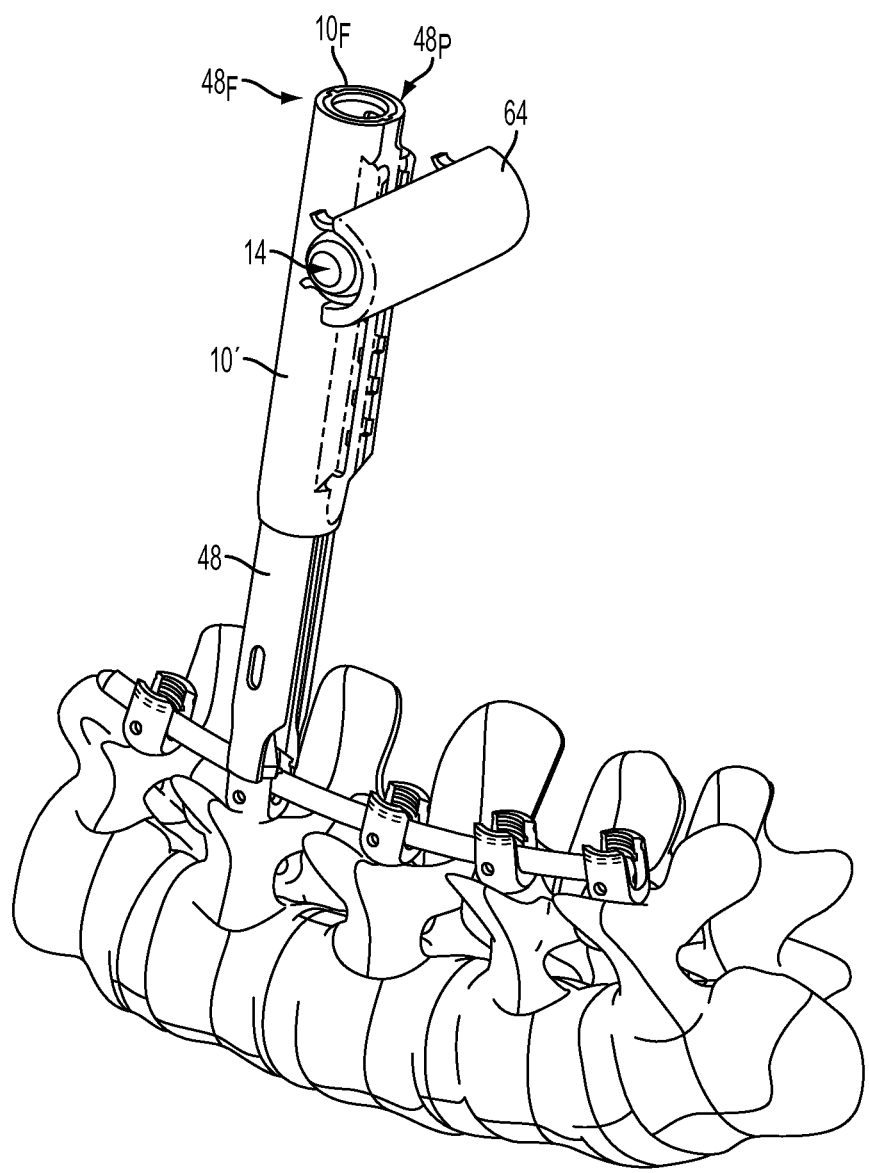
FIG. 4A is a perspective view of an embodiment wherein an insert is coupled to a fulcrum.
Figure 4B:
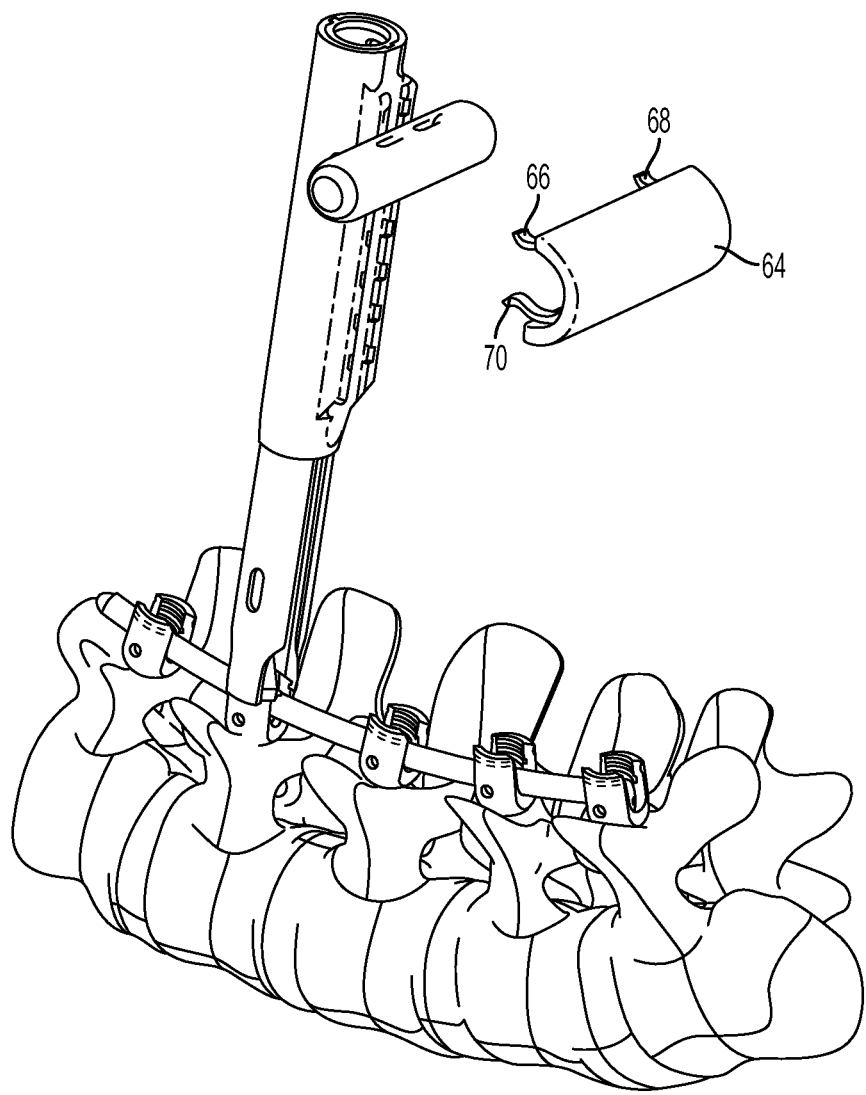
FIG. 4B is a perspective view of the embodiment of FIG. 4A showing the insert disengaged from the fulcrum.
Figure 4C:
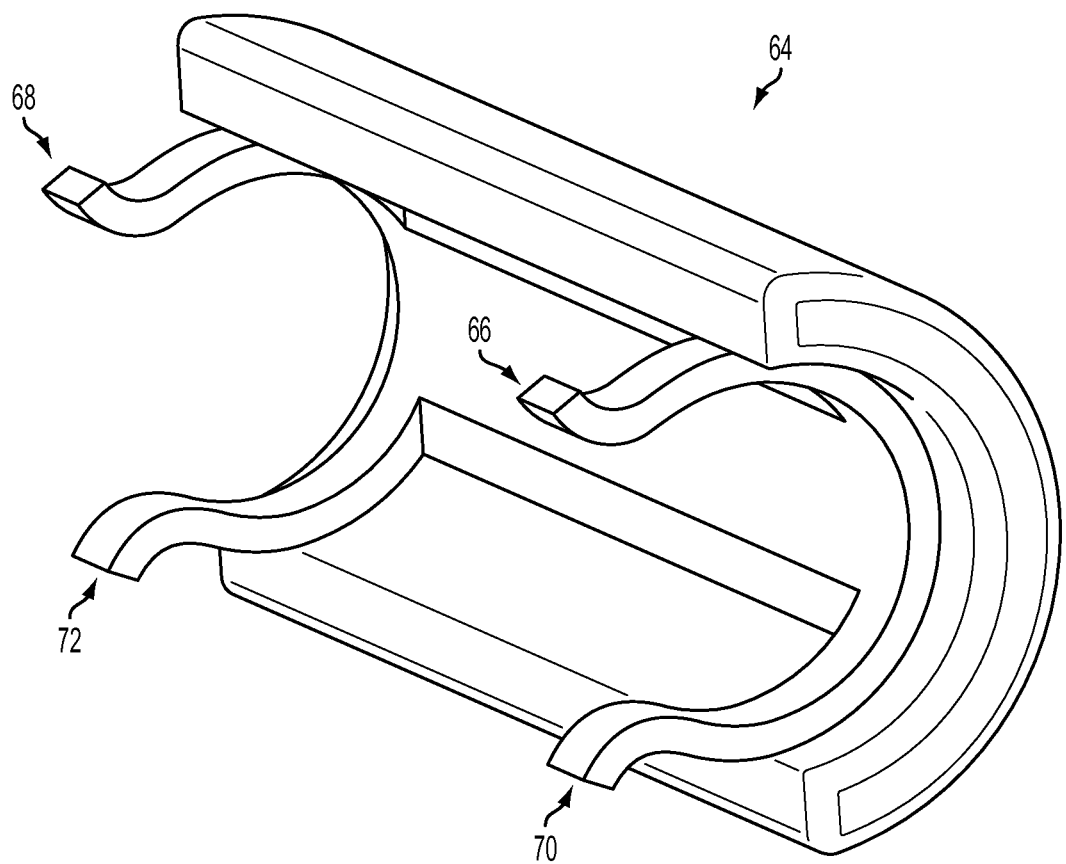
FIG. 4C is a perspective view of an embodiment of the insert of FIG. 4A.

The system also includes a fulcrum that is configured to be movably coupled to some component of the system such that the fulcrum can be easily and reliably positioned at a desired location relative to the adjacent surgical sleeves. In general, the fulcrum can be any such element capable of performing the desired function. For example, FIG. 1A and FIGS. 2A-2E provide an exemplary embodiment of such a fulcrum 14 in relation to first and second surgical sleeves 48, 48'. As shown, the fulcrum 14 can be sized and configured as a cylinder or cylindrical-like element having a longitudinal axis (L') extending therethrough. Also, the fulcrum 14 can have a diameter selected to provide the desired amount of manipulation. In some embodiments, as shown in FIGS. 4A-4C, the diameter of the fulcrum 14 can be increased by coupling an insert 64 to the fulcrum 14. The insert 64 can be coupled to the fulcrum 64 in any of a number of ways. For example, referring to FIG. 4C, the insert 64 can include a plurality of clips 66, 68, 70, 72 configured to releasably engage the fulcrum 14. As will be apparent to those skilled in the art, virtually any element or mechanism capable of modifying the diameter of the fulcrum is within the spirit and scope of the presently disclosed system.

Figure 1B:
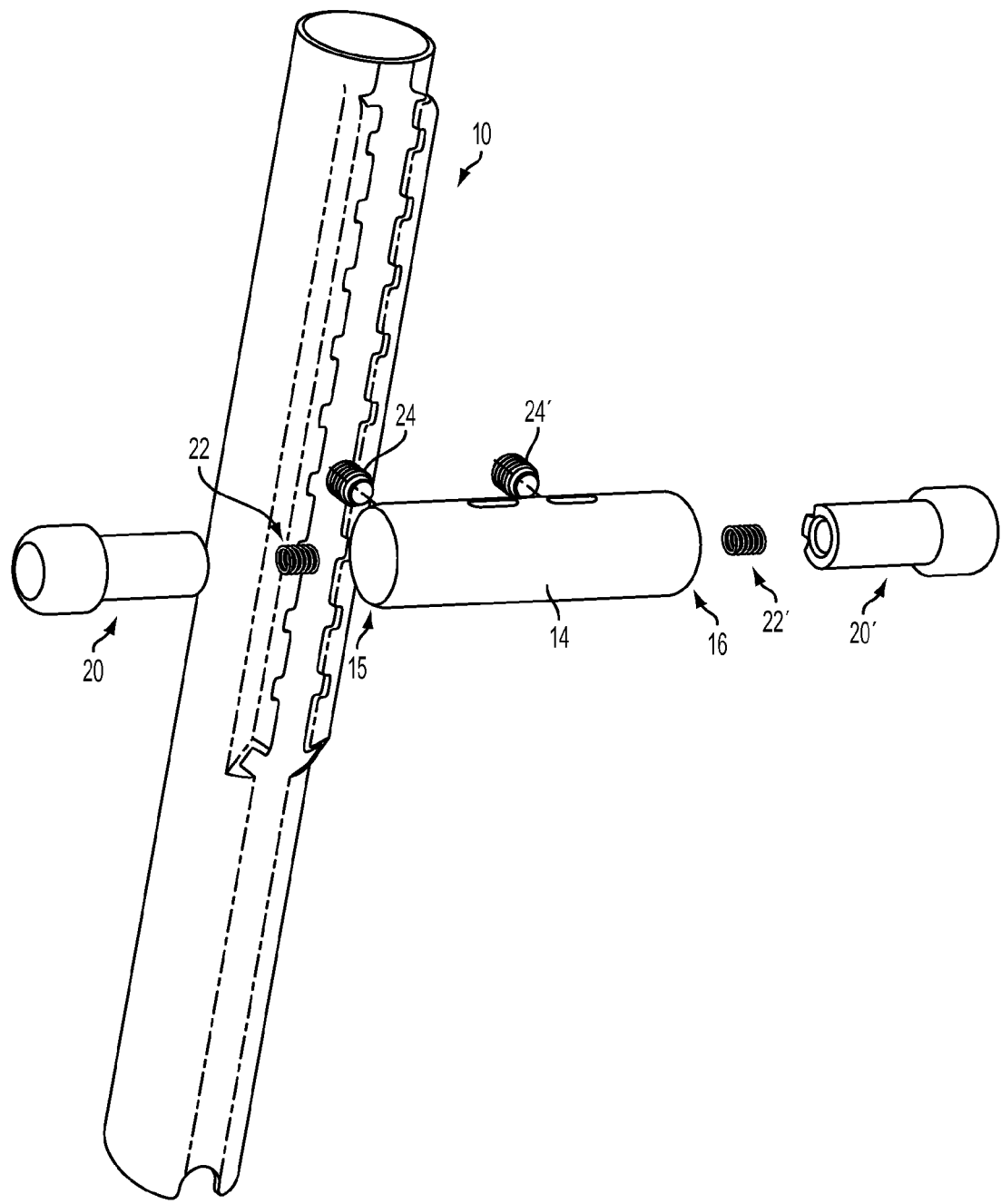
FIG. 1B is a front exploded view of the manipulation device of FIG. 1A.
Figure 1C:
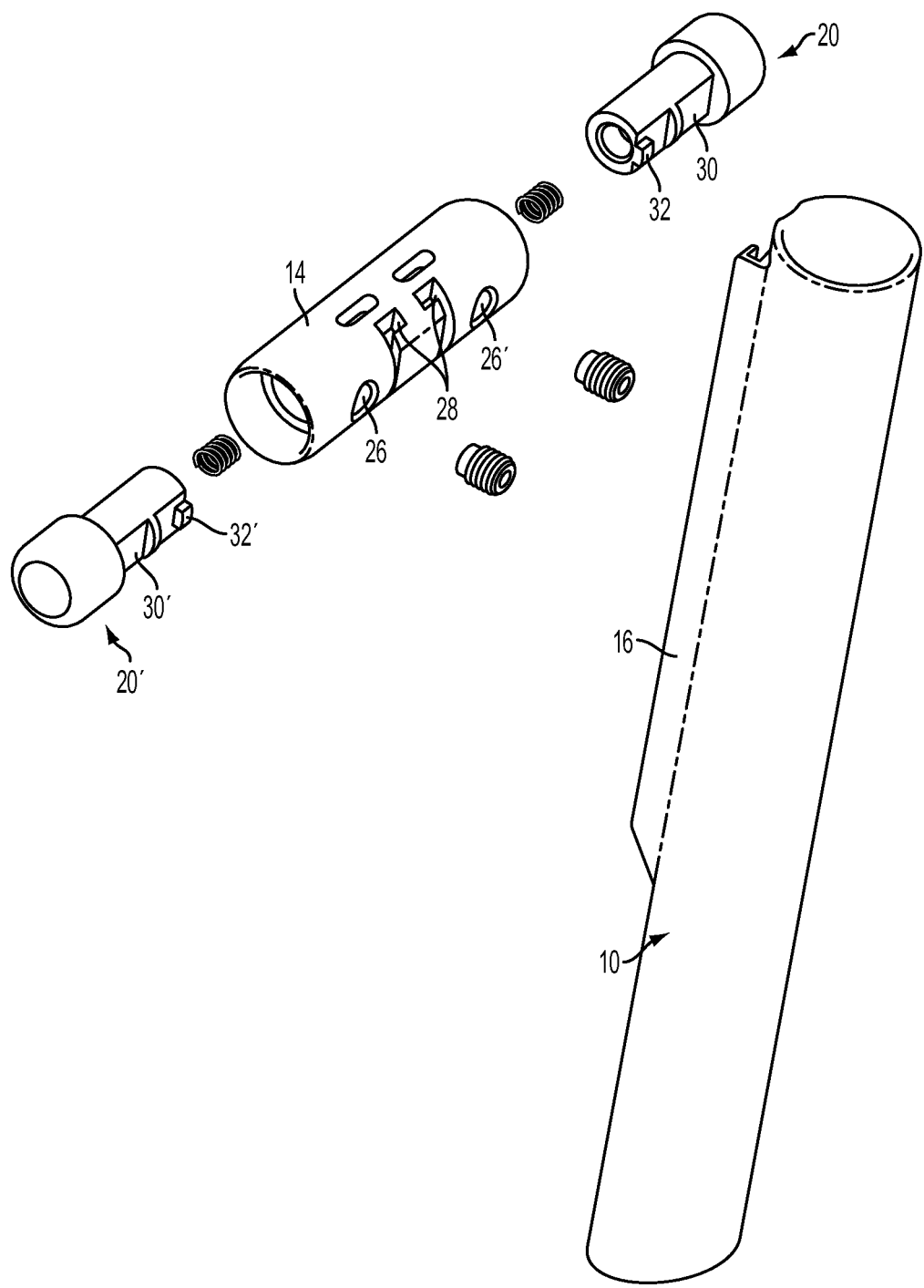
FIG. 1C is a rear exploded view of the manipulation device FIG. 1A.

The system can be configured in various ways to allow the fulcrum to be quickly and accurately secured at any of a number of desired locations relative to the adjacent sleeves 48, 48'. In one such embodiment, the fulcrum 14 can be movably coupled to a manipulation device 10 which is sized and configured to be positioned over a surgical sleeve 48 extending from a vertebra. FIGS. 1A-1C provide an exemplary embodiment of a such manipulation device 10 which includes a proximal end $10_P$, a distal end $10_D$, and an inner lumen extending therebetween which is sized and configured to receive the surgical sleeve 48.

Various embodiments of such a manipulation device 10 are provided herein. In the exemplary embodiment of FIGS. 1A-1C and FIGS. 2A-2E, the manipulation device 10 can include a length $L_1$ substantially identical to the length (l) of the surgical sleeve 48 thereby allowing the manipulation device 10 to extend out of the patient's body from the bone anchor $B_1$. As shown in FIGS. 1A-1C, the distal portion $10_D$ of the manipulation device 10 can include an indentation 12 configured to receive (e.g., straddle) a fixation element 50 disposed within a corresponding bone anchor $B_1$ (also see FIGS. 2A-2E). Such an indentation 12 can help to prevent slippage and/or twisting of the sleeve 10 during any aspect of the procedure. Additionally, positioning the distal end $10_D$ of the manipulation device 10 over the location where the percutaneous access device 48 engages the bone anchor $B_1$ can provide added stability during the fixation procedure (e.g., thereby preventing the surgical sleeve 48 from disengaging the bone anchor $B_1$).

Figure 3A:
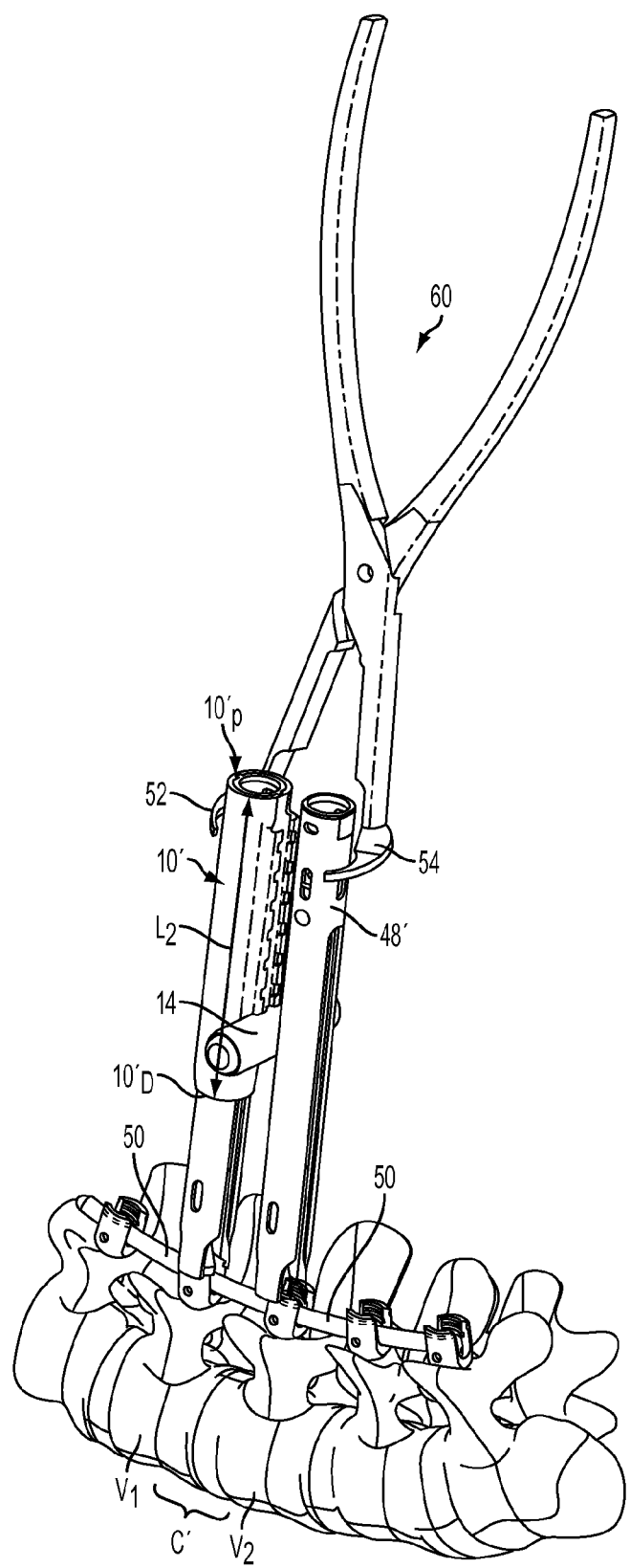
FIG. 3A is a perspective view of an embodiment illustrating a distraction force being applied to adjacent surgical sleeves.
Figure 3B:
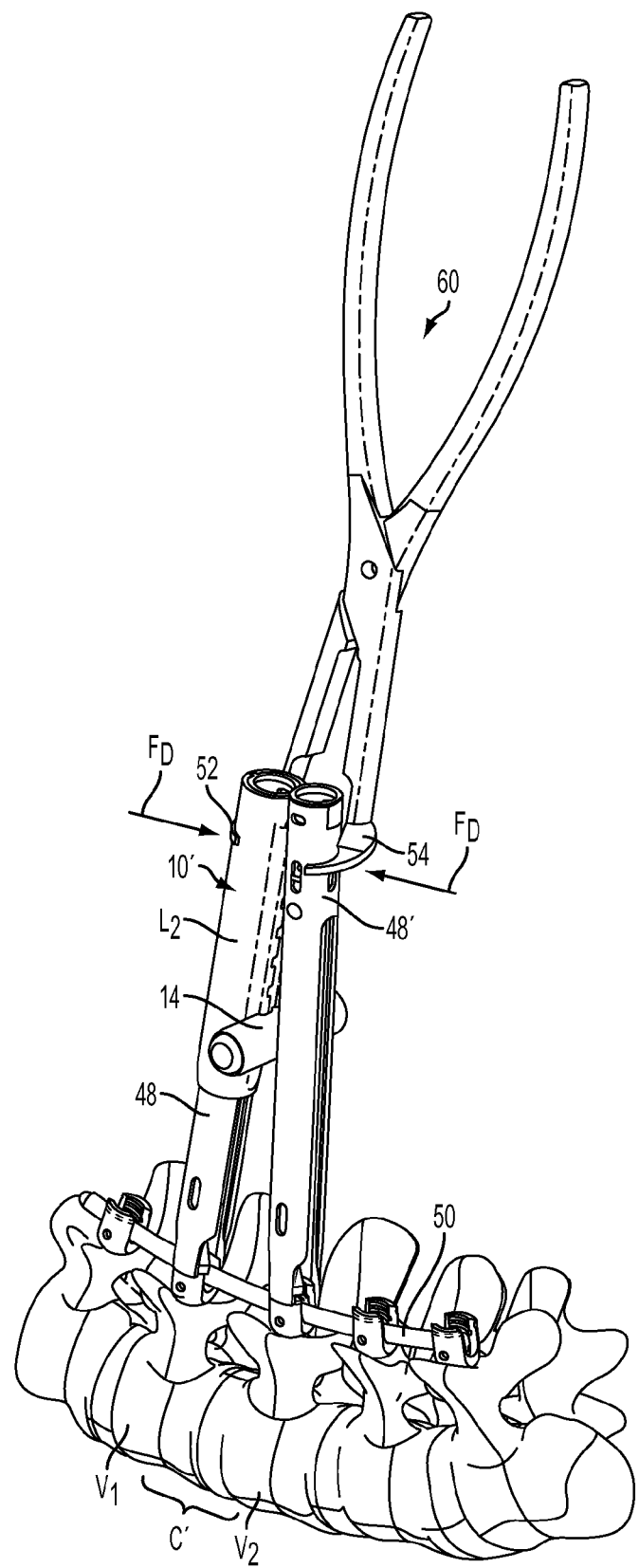
FIG. 3B is a perspective view of the embodiment of FIG. 3A showing distraction of a spinal construct resulting from the distraction force.

FIGS. 3A-3B show an alternative exemplary embodiment wherein the manipulation device 10' includes a proximal end $10'_P$ configured to engage (e.g., abut) a proximal end $48_P$ of the surgical sleeve 48 thereby resulting in the distal end $10'_D$ of the manipulation device 10' residing at a location proximal of the distal end $48_D$ of the surgical sleeve 48. Such an embodiment can be especially useful in those procedures having adjacent surgical sleeves 48, 48' extremely close to one another or even criss-crossing thereby making it difficult to deliver the distal end $10'_D$ of the manipulation device 10' to the distal end $48'_D$ of the surgical sleeve 48'. Like above, this alternative embodiment can be configured in various ways to prevent slipping and/or twisting during any step of the fixation procedure. For example, a proximal region $10'_P$ of the manipulation device 10' can include at least one flat region $10'_F$ corresponding to a flat region $48_F$ formed on the proximal portion $48_P$ of the surgical sleeve 48 thereby preventing any undesired twisting of the manipulation device 10' relative to the surgical sleeve 48. It will be apparent to those skilled in the art that any such mechanism and/or configuration can be utilized to prevent such unwanted movement.

The fulcrum 14 can be movably coupled to the manipulation device 10 in virtually any manner capable of allowing the fulcrum 14 to be moved (e.g., slid) from a first secure position to a second secure position along a length of the sleeve 10. In the exemplary embodiment of FIGS. 1A-1C, the manipulation device 10 can include an engagement track 16 extending along any desired length of the device 10. Further, the engagement track 16 can include any number of engagement points 18, 18', etc. positioned along the length of the engagement track 16. As described below, the fulcrum 14 can be configured to releasably engage any such engagement point 18, 18' to enable the fulcrum 14 to be positioned at any desired location relative to a longitudinal axis (L) of the manipulation device 10. For example, to effect compression of a spinal construct, the fulcrum 14 can be positioned at a proximal position of the engagement track 16 (see FIG. 2C) to allow for a manipulation device to be applied at a location below the fulcrum 14. Alternatively, to effect distraction (see FIG. 3B), the fulcrum 14 can be positioned at a distal end of the engagement track 16 to allow the manipulation force to be applied at a location above the fulcrum 14.

The fulcrum 14 can be slidably coupled to the engagement track 16 in various manners. For example, as shown in FIGS. 1B-1C, the fulcrum 14 can include a first end 15 and a second end 16 wherein at least one end 15, 16 includes an actuator 20, 20' capable of releasing the fulcrum 14 in response to an actuation force. While virtually any type of actuation mechanism can be utilized, in the illustrated exemplary embodiment, each actuator 20, 20' can be configured as a spring-biased button. In such an embodiment, the first and second actuators 20, 20' are in an extended position (i.e., biased apart from one another) in the absence of an actuation force and configured to move to a retracted position in response to the actuation force. In the extended position, the actuators 20, 20' can be configured to securely engage an engagement point 18, 18' along the engagement track 16 thereby securing the fulcrum 14 at a desired location. However, in the retracted position (i.e., in the presence of the actuation force), the actuators 20, 20' can disengage the engagement points 18, 18' thereby allowing the fulcrum 14 to slide from a first position 18 to any other position 18' of the engagement track 16.

As will be apparent to those skilled in the art, such engagement/disengagement mechanisms can be provided in various manners. In the illustrated exemplary embodiment, the fulcrum 14 can include a slot 28 configured to receive the engagement track 16 such that the fulcrum 14 can slide along the track 16 (as indicated by up and down arrows in FIG. 1A). Further, the first actuator 20 can include a first protrusion 32 and the second actuator 20' can include a second protrusion 32'. In the absence of an actuation force, the first and second protrusions 32, 32' can reside within corresponding engagement points 18 (e.g., notches) of the engagement track 16 thereby securing the fulcrum 14 at the desired location. During application of the actuation force, the first and second protrusions 32, 32' can be moved out of the corresponding engagement points 18 thereby allowing the fulcrum 14 to once again slide along the length of the engagement track 16. To provide stability, as illustrated in FIGS. 1B-1C, a first set screw 24 can be placed in communication with the first actuator 20 and a second set screw 24' can be placed in communication with the second actuator 20' thereby contacting corresponding portions 30, 30' of the actuator 20, 20'. Following manufacture, the proximal portion of each set screw can be removed (e.g., by grinding). One skilled in the art will appreciate that rather than being slidable in the track 16, the fulcrum can be removable from the track and repositionable at a desired location.

Figure 5A:
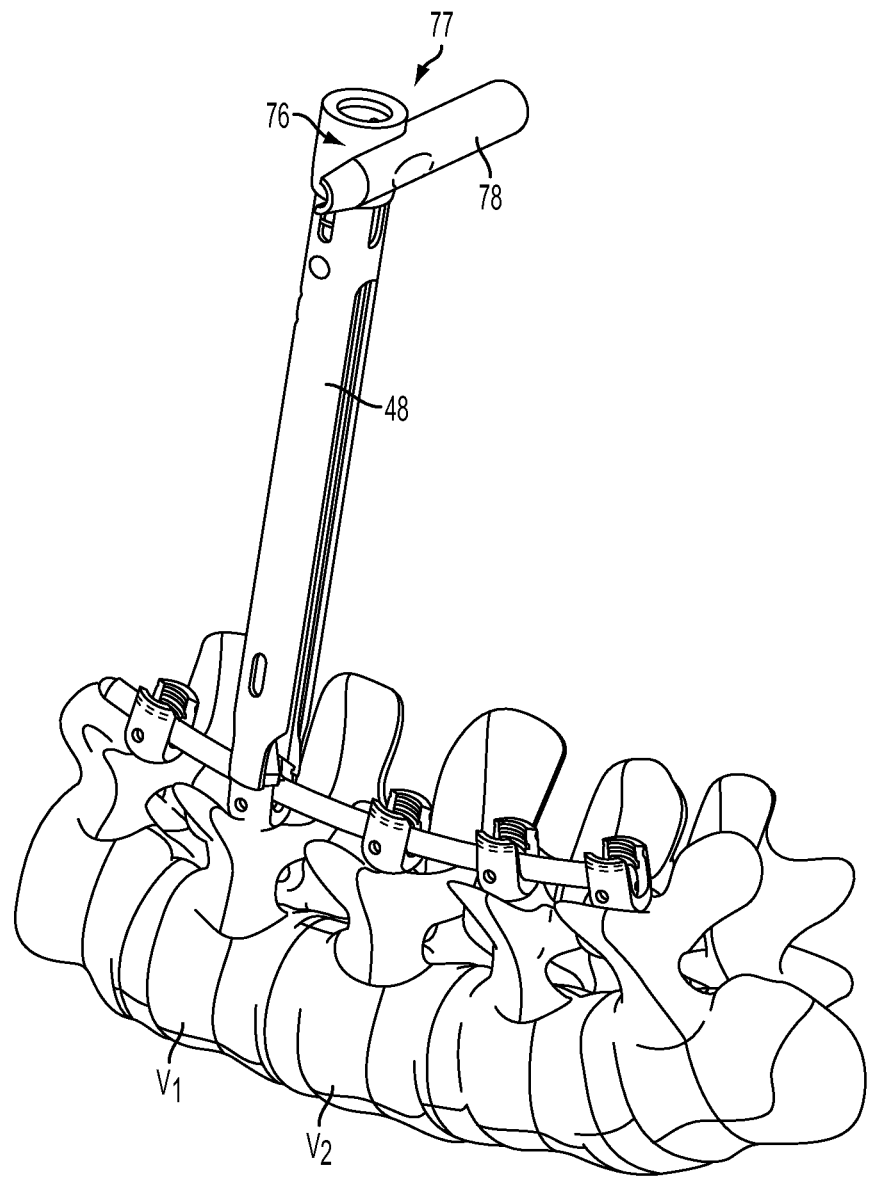
FIG. 5A is a perspective view of another exemplary embodiment of a fulcrum element having a fulcrum releasably coupled to a cap.
Figure 5B:
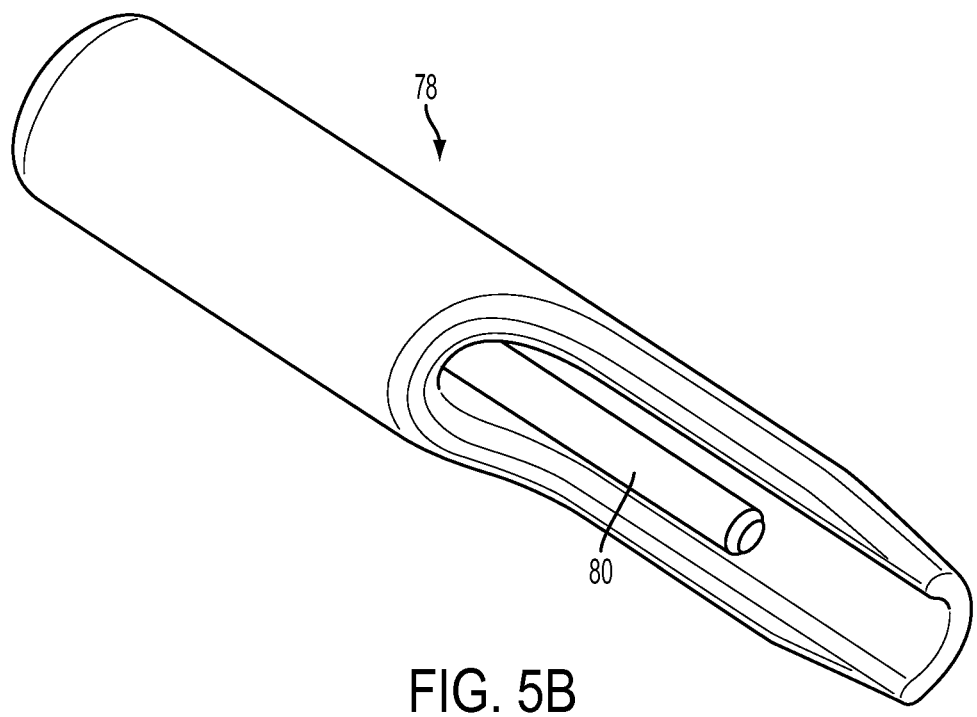
FIG. 5B is a perspective view of the fulcrum of the embodiment of FIG. 5A.
Figure 5C:
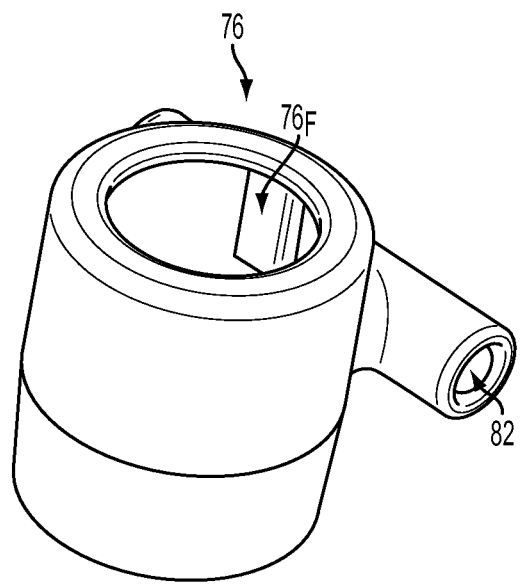
FIG. 5C is a perspective view of the cap of the embodiment of FIG. 5A.

In other embodiments of the system, the fulcrum can be repositionable relative to adjacent surgical sleeves in various other ways. For example, FIGS. 5A-5C provide an alternative exemplary embodiment having a fulcrum element 77 capable of being coupled to a proximal portion of the surgical sleeve 48. More specifically, the fulcrum element 77 can include a cap element 76 sized and configured to be positioned over the proximal end of the sleeve 48. The cap 76 can also include a flat $76_F$ corresponding to a flat region of the surgical sleeve 48 thereby preventing any unwanted movement (e.g., twisting)

during any step of the procedure. As shown in FIGS. 5B-5C, the cap 76 can be configured to releasably engage a fulcrum 78 by inserting an extension 80 of the fulcrum 78 into a corresponding receiving element 82 formed on the cap 82 (or vice versa). In other embodiments, the cap 76 and the fulcrum 78 can be a single component. Like above, this embodiment can allow for the fulcrum 78 to be positioned at any desired position relative to adjacent surgical sleeves 48, 48'. For example, the surgeon can have a plurality of such caps (e.g., a kit) wherein each cap can have a distinct length thereby allowing the fulcrum 78 to be positioned at any number of locations relative to the adjacent sleeves 48, 48'. In another embodiment (not shown), a single cap can be provided which includes a plurality of extensions along a length thereof thereby allowing the fulcrum to engage any of the extensions thereof. Additionally, fulcrums 78 of various diameters can also be provided in order to allow for the desired therapeutic result. Those skilled in the art will appreciate that various other embodiments of engaging the fulcrum along the length of the surgical sleeve can be included within the presently disclosed system. For instance, the surgical sleeve can include a series of openings (not shown) along the length of the device wherein a fulcrum can be configured to slide between the openings and/or be engaged and disengaged from any of the openings.

Figure 6A:
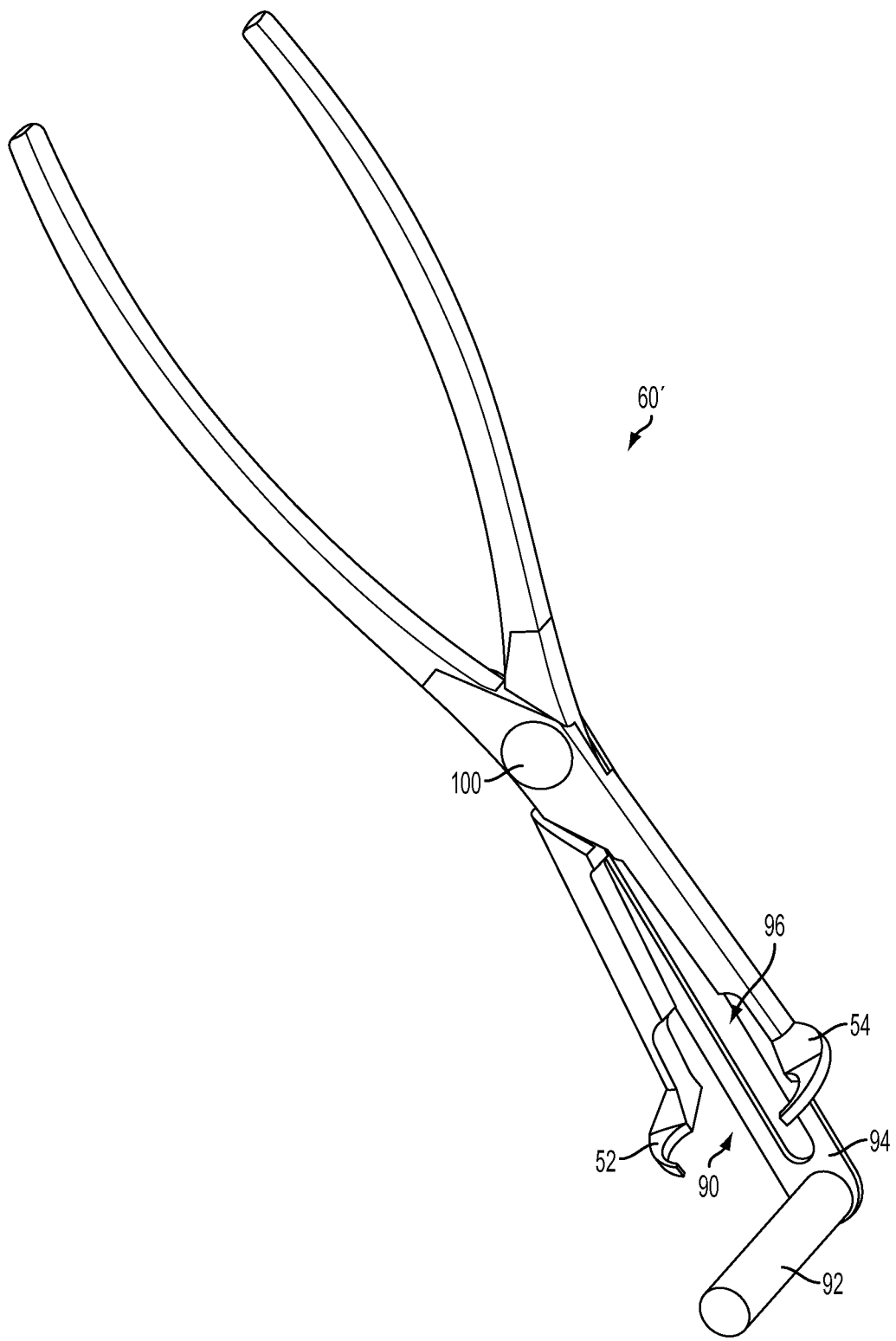
FIG. 6A is a perspective view of another exemplary embodiment wherein a fulcrum is movably coupled to a driver wherein the fulcrum is shown in an extended position.
Figure 6B:
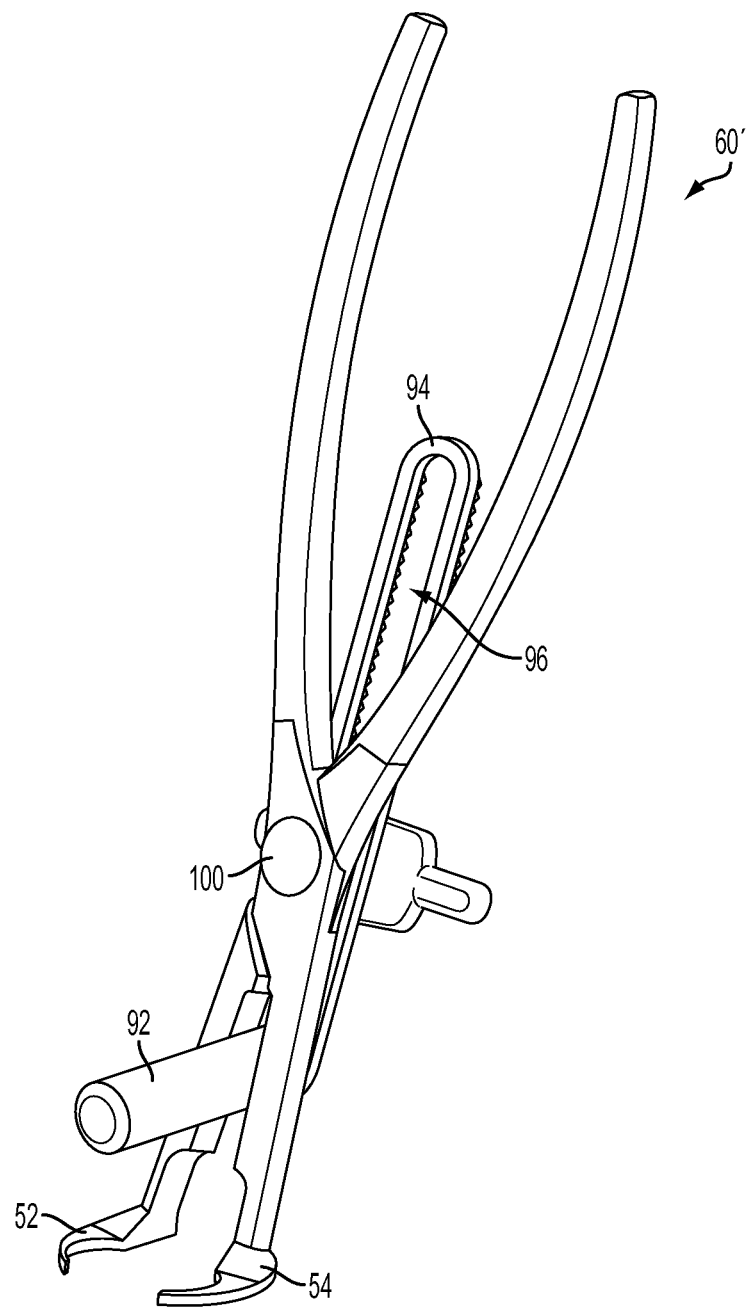
FIG. 6B is a perspective view of the embodiment of FIG. 6A wherein the fulcrum is shown in a retracted position.
Figure 6C:
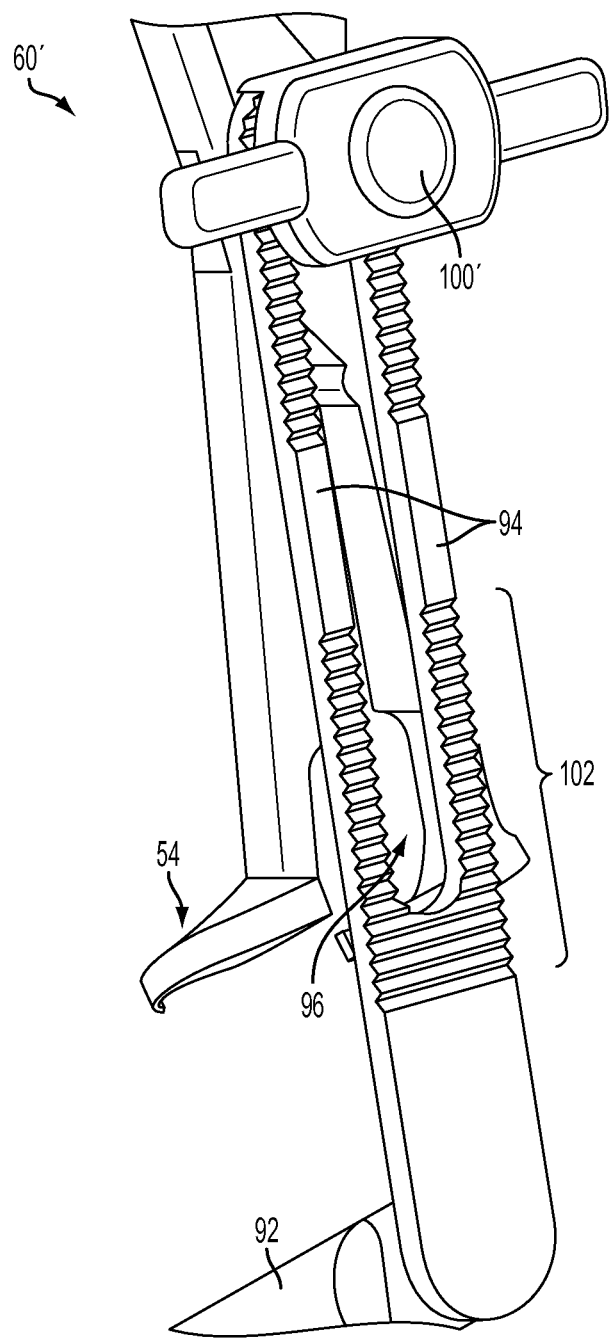
FIG. 6C is a rear view of the embodiment of the driver of FIG. 6A.

In yet another exemplary embodiment, the fulcrum can be movably coupled to a driver thereby allowing the surgeon to easily control the position of the fulcrum relative to the application of the manipulation force on adjacent surgical sleeves. The fulcrum can be movably coupled in any manner to any type of driver. For example, FIGS. 6A-6C provide an exemplary embodiment wherein a driver 60' is a forceps-like instrument having a first extension 52 configured to contact a first surgical sleeve and a second extension 54 configured to contact a second surgical sleeve thereby allowing a manipulation force to be applied to the adjacent sleeves. In such an embodiment, the driver 60' can include a fulcrum 92 coupled thereto such that the fulcrum 92 can be moved between an extended orientation (as shown in FIG. 6A) or a retracted orientation (as shown in FIG. 6B). In the extended orientation, the fulcrum 92 is below the point at which the manipulation force is applied thereby resulting in distraction of a spinal construct. In the retracted position, the fulcrum 92 can be positioned above the point at which the manipulation force is applied thereby resulting in a compression of the spinal construct.

While the fulcrum 92 can be engaged to the driver 60' in virtually any manner capable of allowing the desired movement, FIG. 6C provides an exemplary embodiment which includes an elongate member 94 extending proximally from the fulcrum 92 and having a central channel 96 extending along a length of the member 94. A locking element 100 can be configured to pass through the central channel 96 so as to lock or release the elongate member relative to the driver 60'. Optionally, a plurality of ridges 102 or other type(s) of roughened regions can be incorporated into the elongate member 94 thereby further securing the fulcrum 92 at the desired location.

Additionally, the present disclosure also includes various embodiments of a method of manipulating (e.g., distracting or compressing) a spinal construct. In any such embodiment, the method can include repositioning a fulcrum relative to adjacent surgical sleeves thereby allowing the desired manipulation force to be supplied to the sleeves at a location above or below the fulcrum. Various embodiments of the method can utilize any of the embodiments of the system described above such that, for example, the fulcrum can be movably coupled to a manipulation device, the fulcrum can be movably coupled to the surgical sleeve, the fulcrum can be movably coupled to a driver, etc. Additionally, the methods disclosed herein can be performed as a minimally invasive procedure or as an open procedure.

Figure 2A:
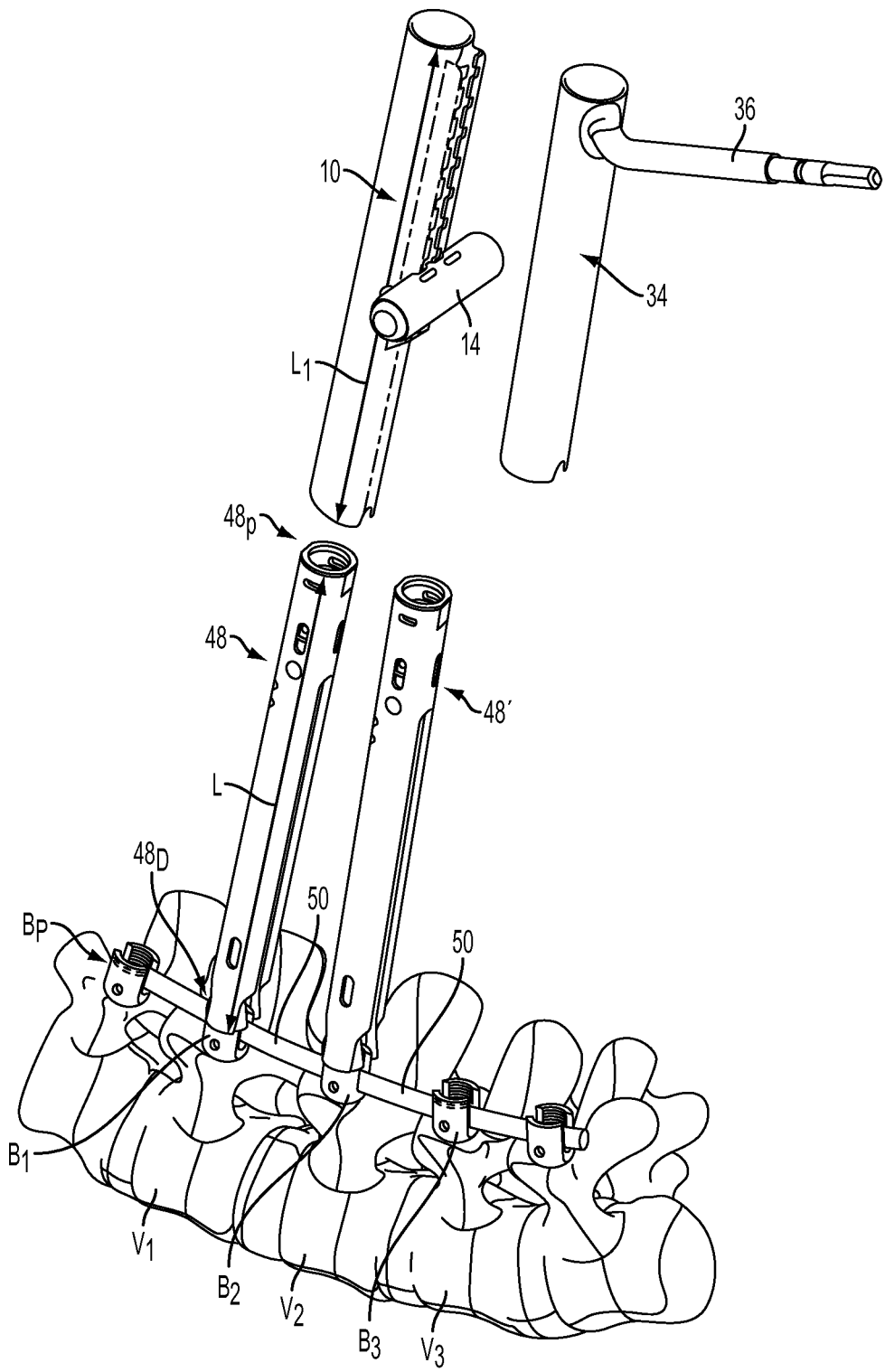
FIG. 2A is a perspective view of a manipulation device and an embodiment of an anti-torque sleeve prior to placement over first and second surgical sleeves.

FIGS. 2A-2E provide an exemplary embodiment of a method for effecting compression of a spinal construct. As shown in FIG. 2A, the method can include engaging a first bone anchor $B_1$ to a first vertebra $V_1$, and engaging a second bone anchor $B_2$ to a second vertebra $V_2$ which is adjacent the first vertebra $V_1$. As will be apparent to those skilled in the art, various embodiments can utilize any number of bone anchors $B_1, B_2, B_3$, etc. along any length of a patient's spinal column. As described below, the use of numerous such sleeves can provide for compression and/or distraction of any number of spinal constructs along any length of a patient's spinal column.

Figure 2B:
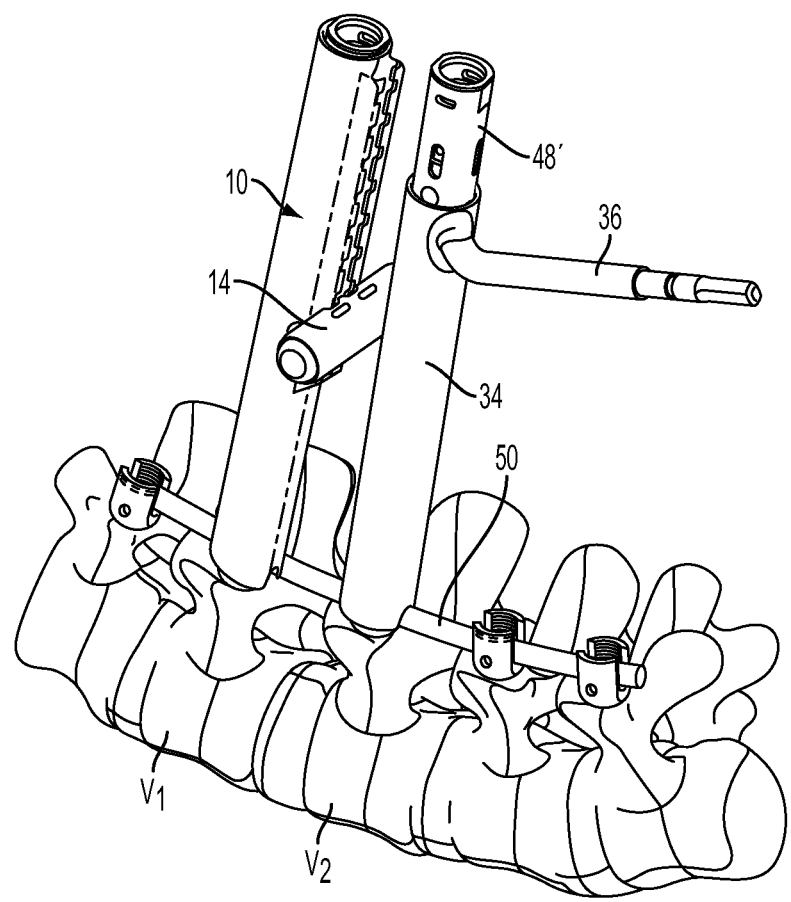
FIG. 2B is a perspective view of the embodiment of FIG. 2A wherein the manipulation device and the anti-torque sleeve are positioned over respective surgical sleeves.

While any of the above-described embodiments of the system can be utilized in the presently disclosed method, FIGS. 2A-2E illustrate the use of a manipulation device 10 having a fulcrum 14 movably (e.g., slidably) coupled thereto. Referring to FIGS. 2A and 2B, the manipulation device 10 can be sized and configured to receive a first surgical sleeve 48 therethrough. Also shown, a second accessory sleeve 34 can optionally be positioned over a second surgical sleeve 48'. As will be apparent to those skilled in the art, the second accessory sleeve 34 can be any of a wide range of such accessory sleeves capable of providing various therapeutic benefits. For example, as shown, the accessory sleeve 34 can be an anti-torque sleeve 34 which can include a handle element 36 extending therefrom. As described, the anti-torque sleeve 34 can allow the surgeon to quickly deliver a closure mechanism (not shown) to the second bone anchor immediately following compression or distraction of the spinal construct (C) thereby securing the fixation element 50 in the desired location. While a wide range of such anti-torque sleeves 34 can be utilized, in this exemplary embodiment, the anti-torque sleeve 34 includes a proximal end, a distal end, and an inner lumen extending therebetween that is sized and configured to receive the second surgical sleeve 48'.

Figure 2C:
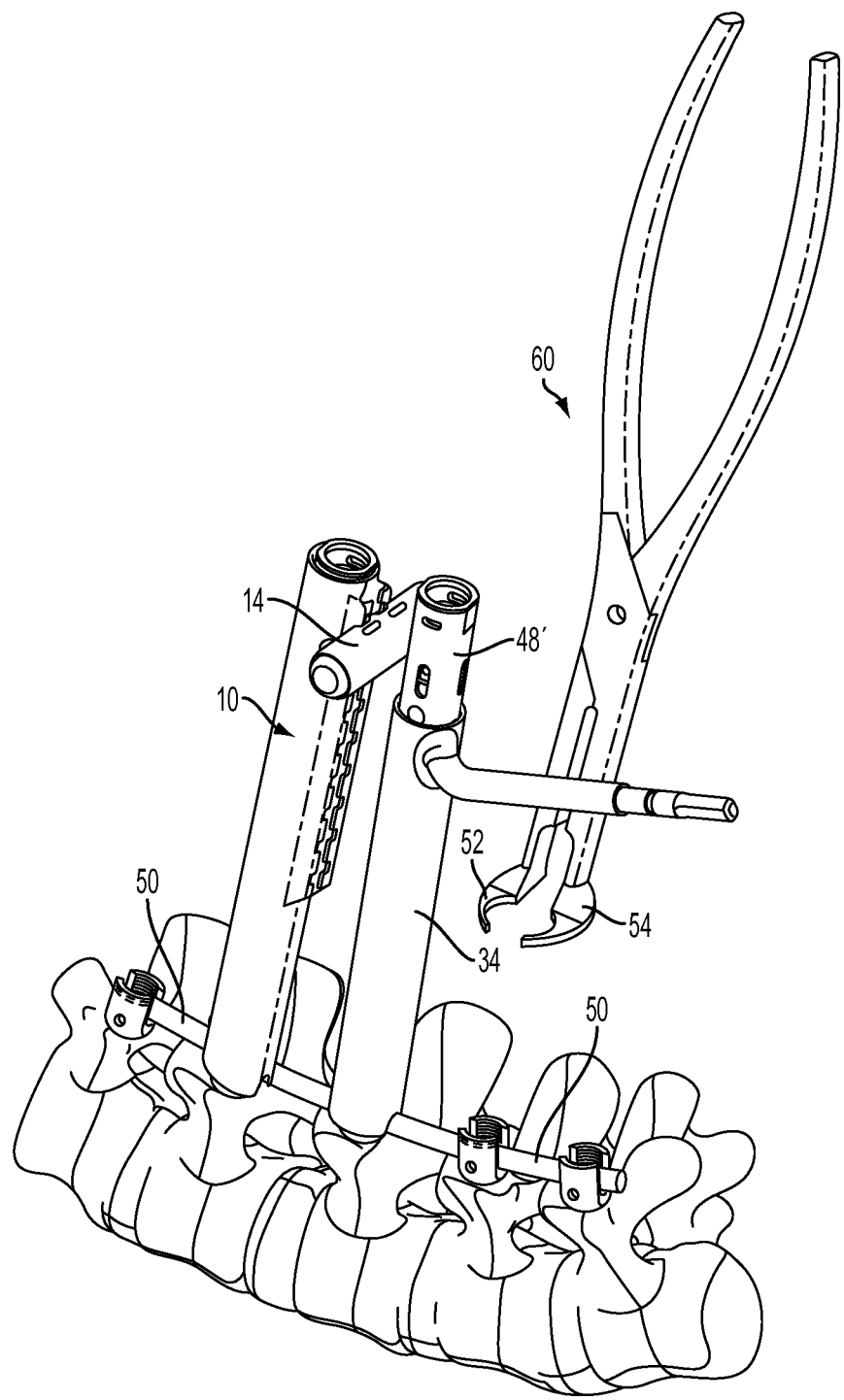
FIG. 2C is a perspective view of the embodiment of FIG. 2A wherein the fulcrum is positioned at a proximal location of the manipulation device.
Figure 2D:
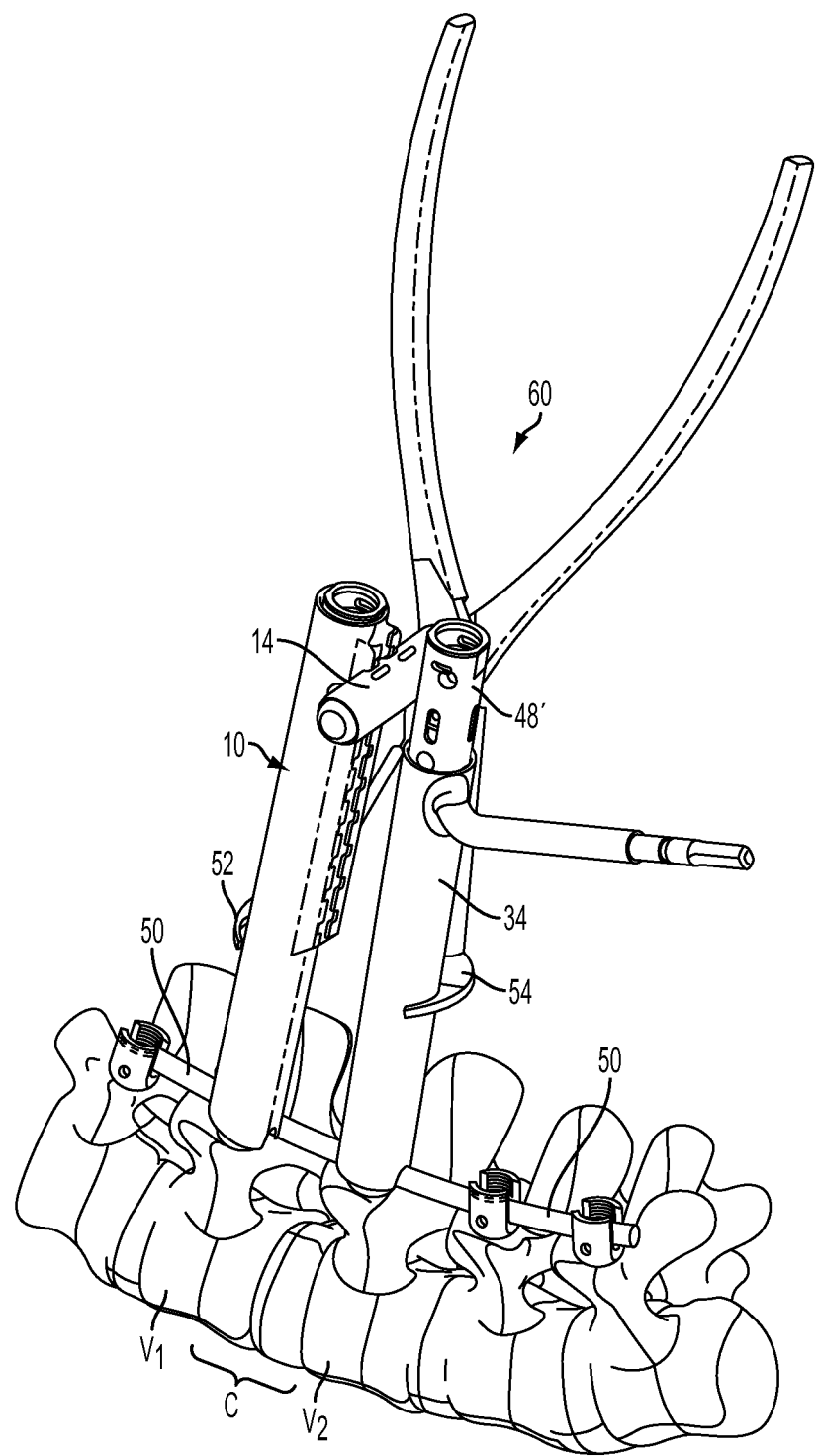
FIG. 2D is a perspective view of the embodiment of FIG. 2A illustrating a driver applying a compression force to the adjacent surgical sleeves.
Figure 2E:
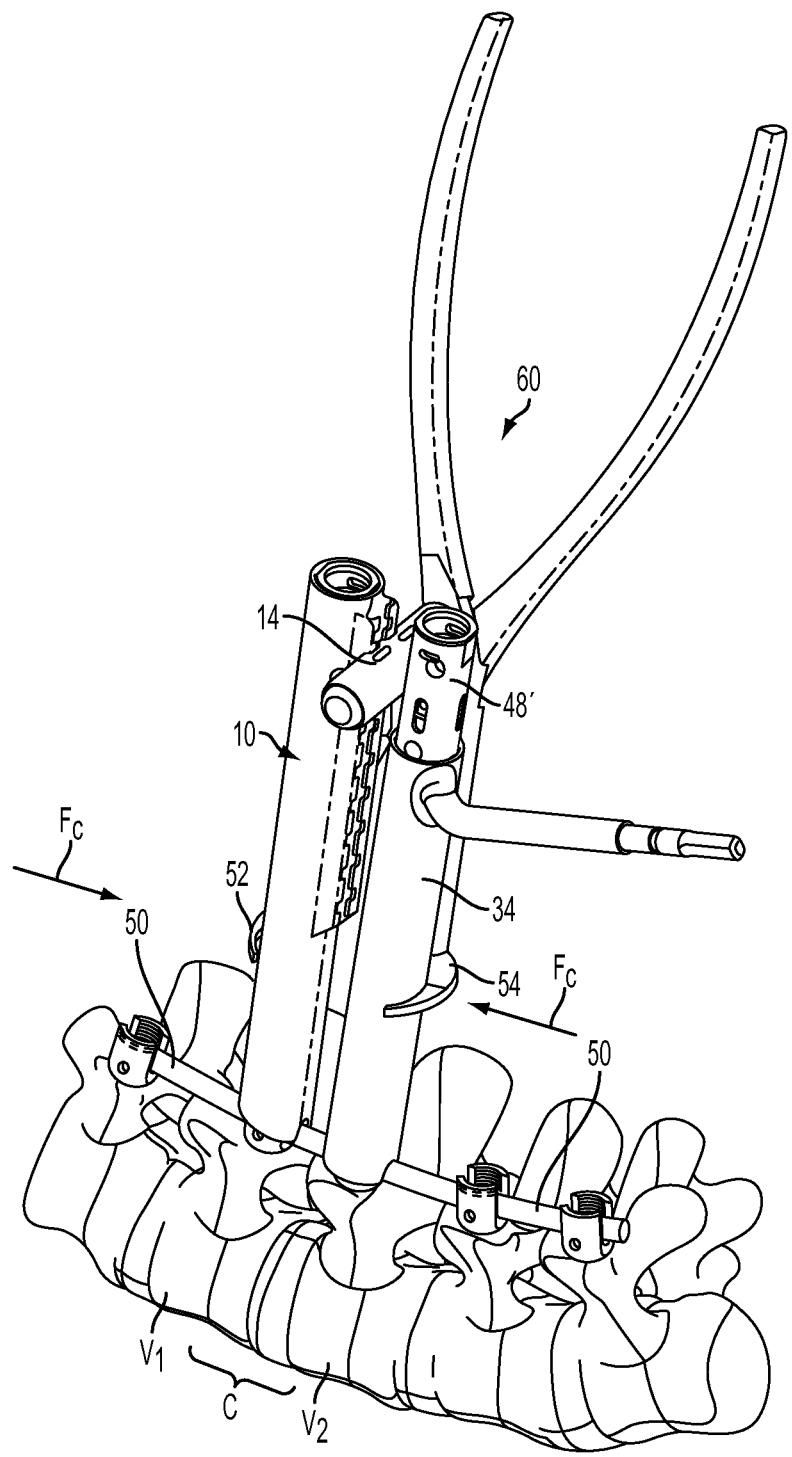
FIG. 2E is another perspective view of the embodiment of FIG. 2A showing compression of the spinal construct resulting from the compression force.

Referring to FIG. 2C, the method can further include determining a desired location for positioning of the fulcrum relative to the adjacent surgical sleeves 48, 48', and subsequently releasably engaging the fulcrum 14 at the location. While the fulcrum 14 can be positioned anywhere along the sleeve 10, in a compression procedure, the surgeon will typically prefer to position the fulcrum 14 as high as possible along the sleeve 10. In such a position, a manipulation instrument 60 can easily provide the desired compression force ($F_C$) at a location below the fulcrum 14 thereby providing an optimal amount of force to the first and second surgical sleeves 48, 48' (as shown in FIGS. 2D-2E). Once complete, a second closure mechanism (not shown) can be secured to the second bone anchor thereby securing the spinal fixation element 50 within the second bone anchor and serving to maintain the effected amount of compression. As indicated above, use of the anti-torque sleeve 34 can allow the surgeon to immediately secure (e.g., tighten or lock) the second closure mechanism thereby preventing any loss of compression that could result from any delay.

In an alternative embodiment, as shown in FIGS. 3A-3B, the method can effect distraction of a spinal construct. In such a procedure, the surgeon will typically prefer to releasably engage the fulcrum 14 as low on the sleeve 10' as possible (i.e., as close to the target spinal construct (C') as possible) thereby providing the optimal distraction force ($F_D$) as the distraction force is applied above the fulcrum 14. Thus, as shown in FIG. 3B, the distraction force ($F_D$) can be applied above the fulcrum 14 thereby distracting the construct C' the desired amount. While an anti-torque sleeve is not shown in FIG. 3B, it will be apparent to those skilled in the art that such a sleeve could be positioned over the second percutaneous access device thereby allowing the surgeon to secure a closure mechanism to the second bone anchor immediately following the desired distraction.

The exemplary embodiments provided above illustrate compression or distraction of a single spinal construct. However, as will be apparent to one skilled in the art, the method can further include effecting compression and/or distraction to any number of vertebrae along any desired length of the patient's spine. For example, in those embodiments utilizing a manipulation device, following compression or distraction of a single spinal construct, the method can include removing the manipulation device from the first surgical sleeve and replacing the anti-torque sleeve (if used) from the second surgical sleeve with the manipulation device. In such an embodiment, the anti-torque sleeve can then be repositioned over a third such surgical sleeve extending from a third vertebra wherein the third vertebra is adjacent the second vertebra. Once positioned as such, the manipulation device can be utilized to deliver a second manipulation force to the manipulation device and the anti-torque sleeve thereby once again effecting a desired compression or distraction upon the second spinal construct. Following the desired manipulation, like above, a third closure mechanism can be secured to the third bone screw thereby once again securing the fixation element within the third bone anchor. As will be apparent to those skilled in the art, all or at least some of these steps can be repeated as many times as desired so as to effect compression and/or distraction of any number of spinal constructs extending along the patient's spinal column.

One skilled in the art will appreciate further features and advantages of the presently disclosed system and method based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A method for manipulating a spinal construct, comprising:
    engaging a first surgical sleeve to a first bone anchor configured to engage a first vertebra;
    engaging a second surgical sleeve to a second bone anchor configured to engage a second vertebra adjacent to the first vertebra;
    delivering a spinal fixation element such that at least a portion of the fixation element resides within the first and second bone anchors;
    adjusting a position of a fulcrum relative to a driver, the fulcrum being movably coupled to one of the first surgical sleeve, the second surgical sleeve, and the driver;
    applying a manipulation force to the first and second surgical sleeves by the driver, the manipulation force capable of causing at least one of the first and the second surgical sleeves to pivot around the fulcrum,
    wherein adjusting the position of the fulcrum with respect to the driver comprises:
        actuating an actuator of the fulcrum to cause the fulcrum to assume a retracted position in which the fulcrum can slide along an engagement track;
        moving the fulcrum to a desired engagement point on the engagement track; and
        releasing the actuator to cause the fulcrum to assume an extended position, thereby securing the fulcrum to the engagement track.

2. The method of claim 1, wherein the manipulation force is applied above the fulcrum to effect distraction of a spinal construct.

3. The method of claim 1, wherein the manipulation force is applied below the fulcrum to effect compression of a spinal construct.

4. The method of claim 1, further comprising: coupling the driver to the surgical sleeve, the driver having the fulcrum movably coupled thereto.

5. The method of claim 4, further comprising: coupling an anti-torque sleeve to the second surgical sleeve.

6. The method of claim 1, wherein the actuator is a spring-biased button.

7. The method of claim 1, wherein the engagement track is formed on the one of the first surgical sleeve, the second surgical sleeve, and the driver to which the fulcrum is coupled.

8. The method of claim 1, wherein the engagement track is a ridge that is configured to be slidably seated within a slot of the fulcrum.

9. The method of claim 1, wherein adjusting the position of the fulcrum with respect to the driver comprises removing the fulcrum from the one of the first surgical sleeve, the second surgical sleeve, and the driver to which the fulcrum is coupled at a first position; and
    re-coupling the fulcrum to the one of the first surgical sleeve, the second surgical sleeve, and the driver to which the fulcrum was coupled at a second position.

10. A method for manipulating a spinal construct, comprising:
    placing a first bone anchor in a first vertebra, the first bone anchor having a first percutaneous access device coupled thereto;
    placing a second bone anchor in a second vertebra that is adjacent to the first vertebra, the second bone anchor having a second percutaneous access device coupled thereto;
    placing a spinal fixation element within the first and the second bone anchors;
    positioning a manipulation device over the first percutaneous device, the manipulation device having a fulcrum movably coupled thereto via an engagement track formed along a length of the manipulation device such that the fulcrum is configured to releasably engage the manipulation device at an engagement point of the engagement track;
    engaging a closure mechanism to the first bone anchor to secure the spinal fixation element within the first bone anchor;
    positioning an anti-torque sleeve over the second percutaneous access device;
    positioning the fulcrum element at a desired engagement point along a length of the engagement track;
    applying a force to the manipulation device and the anti-torque sleeve to cause at least one of the manipulation device and the anti-torque sleeve to pivot about the fulcrum; and
    engaging a second closure mechanism to the second bone anchor to secure the spinal fixation element within the second bone anchor.

11. The method of claim 10, further comprising:
    removing the manipulation device from the first percutaneous access device;

removing the anti-torque sleeve from the second percutaneous access device;
repositioning the manipulation device over the second percutaneous access device;
repositioning the anti-torque sleeve over a third percutaneous access device having a distal portion engaged to a third bone anchor;
applying a second manipulation force to the manipulation device and the anti-torque sleeve to cause at least one of the manipulation device and the anti-torque sleeve to pivot about the fulcrum; and
engaging a third closure mechanism to the third bone anchor to secure the spinal fixation element within the third bone anchor.

12. The method of claim 10, further comprising adjusting a position of the fulcrum relative to the manipulation device by sliding a locking element within the engagement track.

13. The method of claim 12, further comprising locking the fulcrum in place relative to the manipulation device by engaging the locking element with at least one of a plurality of ridges formed along the engagement track.

14. A method for manipulating a spinal construct, comprising:
engaging a first surgical sleeve to a first bone anchor configured to engage a first vertebra;
engaging a second surgical sleeve to a second bone anchor configured to engage a second vertebra adjacent to the first vertebra;
delivering a spinal fixation element such that at least a portion of the fixation element resides within the first and second bone anchors;
adjusting a position of a fulcrum relative to a driver, the fulcrum being movably coupled to one of the first surgical sleeve, the second surgical sleeve, and the driver;
applying a manipulation force to the first and second surgical sleeves by the driver, the manipulation force capable of causing at least one of the first and the second surgical sleeve to pivot around the fulcrum,
wherein adjusting the position of the fulcrum with respect to the driver comprises:
applying an actuation force to the fulcrum to slide the fulcrum along a ridge formed on the one of the first surgical sleeve, the second surgical sleeve, and the driver to which the fulcrum is coupled; and
engaging the fulcrum with one or more notches formed at a desired point along the ridge to thereby lock the fulcrum in place along the ridge.

15. A method for manipulating a spinal construct, comprising:
engaging a first surgical sleeve to a first bone anchor configured to engage a first vertebra;
engaging a second surgical sleeve to a second bone anchor configured to engage a second vertebra adjacent to the first vertebra;
delivering a spinal fixation element such that a least a portion of the fixation element resides within the first and second bone anchors;
adjusting a position of a fulcrum relative to a driver, the fulcrum being movably coupled to one of the first surgical sleeve, the second surgical sleeve, and the driver;
applying a manipulation force to the first and second surgical sleeves by the driver, the manipulation force capable of causing at least one of the first and the second surgical sleeve to pivot around the fulcrum,
wherein the fulcrum is movably coupled to the driver via an elongate member extending from the fulcrum, and adjusting the position of the fulcrum with respect to the driver comprises:
sliding a locking element of the driver within a channel of the elongate member; and
engaging the locking element of the driver with at least one of a plurality of ridges formed within the channel to thereby lock the fulcrum in place within the channel.

* * * * *